(12) United States Patent
Sudeith et al.

(10) Patent No.: US 7,381,154 B1
(45) Date of Patent: Jun. 3, 2008

(54) HEART RATE MONITORS AND DISPLAYS FOR CLIMBING WALLS

(75) Inventors: Timothy S. Sudeith, Edina, MN (US); Mertyce Mrvos, Edina, MN (US); Lyle Helke, Marine on St. Croix, MN (US)

(73) Assignee: Everlast Climbing Industries, Inc., Mendota Heights, MN (US)

( * ) Notice: Subject to any disclaimer, the term of this patent is extended or adjusted under 35 U.S.C. 154(b) by 64 days.

(21) Appl. No.: 11/286,458

(22) Filed: Nov. 23, 2005

Related U.S. Application Data

(60) Provisional application No. 60/630,719, filed on Nov. 24, 2004.

(51) Int. Cl.
*A63B 17/00* (2006.01)
*A63B 71/00* (2006.01)
(52) U.S. Cl. ............................................ 482/37; 482/8
(58) Field of Classification Search ............ 482/35–37, 482/51, 52, 1–9, 53–57
See application file for complete search history.

(56) References Cited

U.S. PATENT DOCUMENTS

| D254,569 S | 3/1980 | Moffat et al. |
| 4,848,737 A * | 7/1989 | Ehrenfield .................... 482/52 |
| 5,254,058 A | 10/1993 | Savigny |
| 5,337,753 A | 8/1994 | Lekhtman |
| 5,732,954 A * | 3/1998 | Strickler et al. ............. 273/441 |
| 5,738,104 A * | 4/1998 | Lo et al. ...................... 600/521 |
| 5,944,634 A | 8/1999 | Neves |
| 6,074,327 A | 6/2000 | Franklin |
| 2003/0013072 A1* | 1/2003 | Thomas ....................... 434/247 |
| 2003/0060333 A1* | 3/2003 | Sudeith ........................ 482/37 |

* cited by examiner

*Primary Examiner*—Fenn C. Mathew
(74) *Attorney, Agent, or Firm*—Anthony G. Eggink; Katrina M. Eggink

(57) ABSTRACT

A heart rate monitor assembly for use in a climbing wall assembly. The assembly includes heart rate monitor devices and heart rate display units for climbers. The monitors, display devices, and pulse sensors may be incorporated into the climbing wall structure, hand holds, and/or the wall or route plates mounted on the climbing wall.

18 Claims, 2 Drawing Sheets

HEART RATE MONITORS AND DISPLAYS FOR CLIMBING WALLS

This invention claims the benefit of U.S. Provisional Application Ser. No. 60/630,719, filed on or about Nov. 24, 2004.

BACKGROUND OF THE INVENTION

The present invention relates generally to monitoring and display devices for body function data generated during exercise. Particularly, the invention relates to heart rate monitoring and display devices used in conjunction with climbing walls. More particularly, the invention relates to climbing wall structures, climbing wall panels, hand holds and associated components having heart rate measuring and display devices.

While exercising various bodily functions may be monitored because of the changes that occur during such an exercise. For example, heart rate monitors may be used to measure heart rate, i.e., in beats/minute. During cardiovascular activity, for example, blood pressure, calorie usage, time and heart rate may all be of interest. A participant may thereby assess current activity level as well as progress towards a particular physical health goal. It is desirable, for example, to use heart rate monitors in physical education classes. Heart rate monitors may help students become aware and to take responsibility for their effort while enabling teachers and others to evaluate the progress of the participants.

Artificial climbing and bouldering walls are increasingly used due to physical fitness awareness generally and the interest in climbing and bouldering sports, specifically. Climbing wall assemblies are also provided to introduce children and adults to the climbing sports in a safe, convenient and educational manner. Various devices have also been introduced to make climbing for children and adults educational and informative. Exemplary climbing wall assemblies and devices are disclosed in Applicant's pending U.S. patent application having Ser. No. 10/236,728, filed on Sep. 6, 2002, and in the patent application entitled Safety Mat Securement Assembly having Ser. No. 11/061,583 filed on Feb. 18, 2005, the teachings of which being fully incorporated by reference herein.

Because the climbing sports have increased in popularity, it is therefore also desirable to utilize body function monitors, such as heart rate monitors, for example, when engaging a climbing route on a climbing wall. There is a need in the recreational climbing sport industry to provide heart monitoring, sensor, and display devices to climbers. The heart rate monitors, sensors and displays of the present invention are constructed and arranged to satisfy this need.

SUMMARY OF THE INVENTION

The heart rate monitors and displays of the present invention are directed to climbing activities generally and artificial climbing walls particularly. Hand holds, climbing walls and wall or route plates are provided having sensors which detect and/or record the heart rate of the climber, for example, and display units are provided on the hand hold structures, wall plates and/or on the climbing wall itself to permit both the climber and the teacher or climbing partner to view the heart rate or other physical data. Further, computer interface systems may be incorporated into or utilized with the monitors and displays of the invention to record, store and evaluate a particular climber's body function data or parameters, goals and history.

The invention further provides hand hold structures with removable display devices which may be used in cooperation with chest strap transmitters worn by the climber to monitor and transmit the climber's heart rate. Heart rate hand holds and other monitors and displays are preferably provided at the start, in the middle and at the end of a climbing route.

The heart rate displays may be incorporated into or removable from the hand hold structure. The removal of the display unit is to prevent damage and/or loss when the unit is not being utilized. Known wrist strap or "watch style" heart rate monitors may also be incorporated into the hand hold structures. Hand hold structures may also be provided having the capability to function as a stopwatch, calorie expenditure counter, heart rate high/low limit alarms as well as other data display and recording features.

These and other benefits of this invention will become clear from the following description by reference to the drawings.

DESCRIPTION OF THE PREFERRED EMBODIMENTS

The heart rate monitor, sensor and display devices of the present invention are constructed and arranged for use with climbing wall structures. Although heart rate monitors, sensors and heart rate display units are shown and discussed in this application, the utilization of other bodily data generated during physical activity, i.e., blood pressure, calorie usage and the like, are also within the purview of the present invention.

The heart rate hand holds of the invention are specially designed hand hold structures that house, contain or hold the heart rate display and/or the heart rate sensor. The monitors and display units of the invention are preferably battery operated. The display units are preferably large and easy to read so that the climber's heart rate can be viewed from a distance away from the climbing wall. The display units make it easy for the teacher or climbing partner to view, monitor and record the user's heart rate. Additionally, utilizing a computer interface system, the computer system may be utilized to track each student's heart rate and/or other body function data in a climbing class. Heart rate data collected over time is valuable for goal setting and evaluation.

Figure 1:
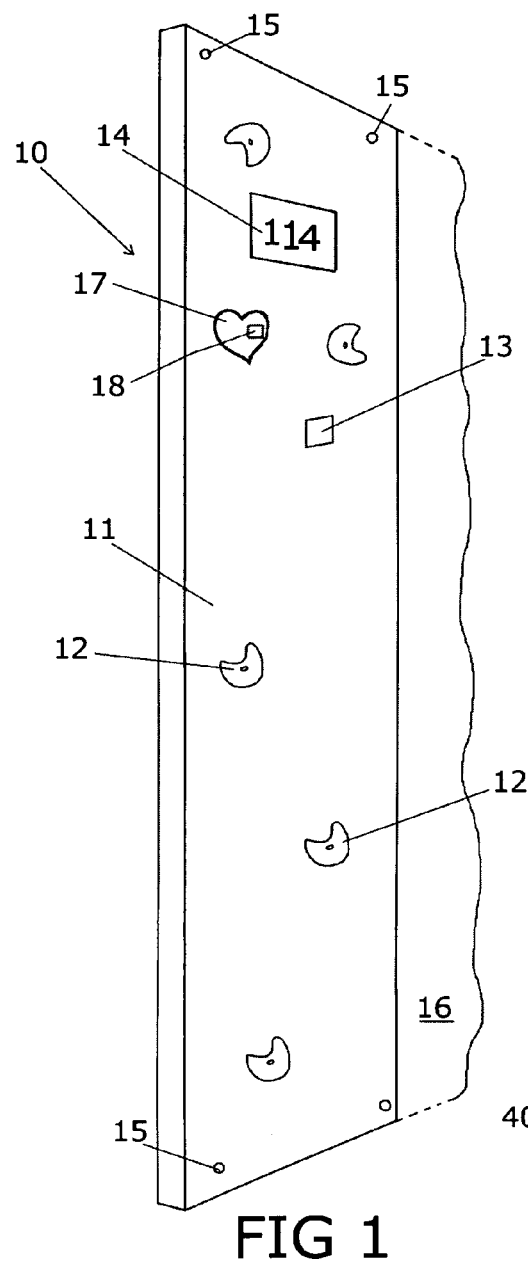
FIG. 1 is a side sectional view of a climbing wall heart rate sensor and display assembly of the present invention.

Referring to FIG. 1, sensor and display assembly 10 is shown comprising a climbing wall panel 11 secured by fasteners, such as bolts 15, to an existing wall structure 16. The climbing wall panel 11 has hand hold structures 12 and 17 mounted thereon and a heart rate sensor 13 and heart rate display 14 incorporated thereinto. The display 14 may be a digital unit that is frictionally or otherwise held within a cavity of the hand hold structure 12. For example, heart-shaped hand hold 17 is shown having sensor or display 18 disposed in or held within a cavity of hand hold 17. The climber and/or teacher may monitor the climber's heart rate or other data by viewing the monitor during the course of the climb.

Figure 2:
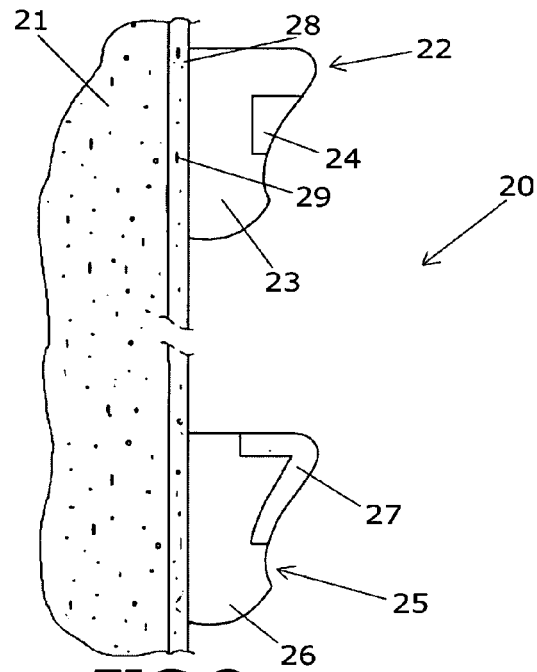
FIG. 2 is a side sectional view of a hand hold heart rate sensor and display assembly of the present invention.
Figure 4:
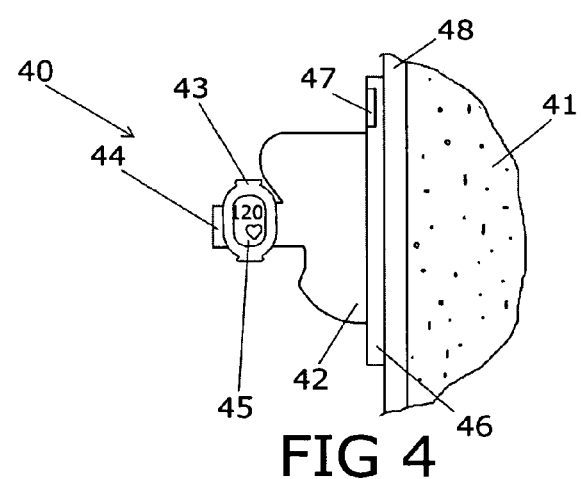
FIG. 4 is a side plan view of a wall plate heart rate sensor device and a hand hold configured to receive a wrist strap heart rate sensor and display device of the present invention.

The climbing wall structure may be comprised of a freestanding structure, a wall panel structure 11 which is mounted to a substructure, as shown in FIGS. 2 and 4, by elements 21 and 41, respectively, or other climbing wall surface provided on a substructure, such as a concrete block wall, for example. The wall sensor and display assemblies of the present invention may be utilized on any such climbing wall structures. A plurality of hand holds are set on climbing walls to create climbing routes which may provide various degrees of difficulty. Route or wall plates may be provided to aid in identifying predetermined climbing routes and to provide various recreational and educational challenges to the climber, as set forth in the above referenced pending '728 and '583 applications. The controlled climbing activities provided by the use of specified wall structures, hand hold structures, hand hold placement and associated route plates permit the body function monitors and displays to be utilized in a beneficial manner for climbers.

FIG. 2 shows a climbing wall substructure 21 having surface 28 thereon and having a hand hold structure 25 having body 26 with a pulse-sensor device 27 incorporated thereon and hand hold structure 22 having body 23 with pulse display 24 incorporated thereon. The sensor device 27 is made part of the hand hold structure and may be used in cooperation with display unit 24 or other display units that are positioned into the same or another hand hold structure or one that is positioned on a wall plate or the climbing wall structure itself. The pulse sensor device 27, when touched by a climber's fingers measures and transmits the pulse rate, or other data obtained, to a display unit visible to the climber. Climbing wall surface 28 is shown disposed on climbing wall substructure 21 and having magnetic or metallic particles 29 incorporated therein. For example, climbing wall surface 28, other climbing wall surfaces, wall plate surfaces and hand hold surfaces may be painted or coated with a layer having magnetic or metallic particles therein. The magnetic or metallic qualities of these surfaces permit a body function data sensor or display assembly having a metallic or magnetic body to be attached to the climbing wall surfaces, wall plate surfaces and hand hold surfaces.

Figure 3:
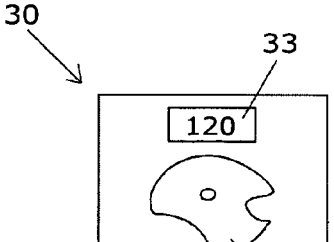
FIG. 3 is a front plan view of a wall plate heart rate monitoring assembly of the present invention.

FIG. 3 shows wall plate display assembly 30 having hand hold structure 32 and wall plate or activity plate 31 having a heart rate display 33 incorporated thereinto. The display 33 is shown to read 120 beats/minute and may be mounted within the removable activity plate 31. The surfaces of the wall structures, wall panels and wall plates may also be a writable surface, i.e., having whiteboard or chalkboard qualities, to permit a climber to mark heart rate or other body function data during the course of a climb.

FIG. 4 shows a climbing wall 41 having exterior surface 48 having wall plate 46 mounted thereon and display assembly 40 having a hand hold structure 42 with a peg or protrusion 44 onto which a wrist strap or watch 43 with display 45 may be positioned for use. Thus, known display structures, i.e., wrist straps or watches, may be utilized and/or incorporated into the hand holds or other elements of a climbing wall structure. The display 45 of watch 43 may be used by a climber utilizing hand hold 42. Pulse sensor 47 is further shown mounted on wall plate 46.

In FIG. 1, fasteners known in the art, i.e., T-nuts and cooperating bolt structure, are shown utilized to mount the climbing wall panels to the existing wall structure. The hand holds and sensor and display devices may be similarly attached to the wall panel structure. In FIG. 2, fasteners known in the art, i.e., expandable sleeve anchor/screw combinations or bolt/nut combinations that extend through the wall and other fastening systems, may be utilized to mount the sensor and display devices to the wall substructure.

In operation, the students or climbers may wear a chest strap or wrist transmitter and as they climb, their heart rate may be displayed on the heart rate hand holds along the wall or on a separate display on a wall plate or on the wall itself. There may be a hand hold at the start of the climbing wall, in the middle and at the end of the climbing course. During the climb, students can pause for a couple of seconds near the heart rate hand hold and the heart rate is automatically displayed. The display may be removable from the heart rate hand hold and/or climbing wall after class, to avoid damage or loss.

Figure 5:
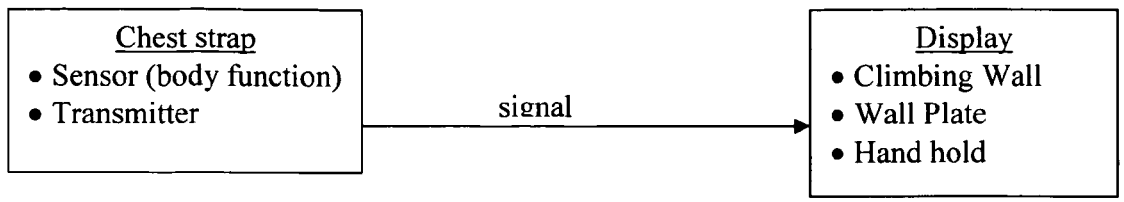
FIG. 5 is a block diagram of a heart rate sensor and display assembly using a chest strap.
Figure 6:
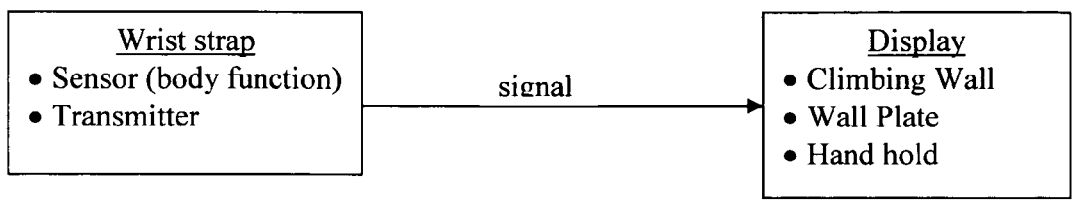
FIG. 6 is a block diagram of a heart rate sensor and display assembly using a wrist strap.
Figure 7:
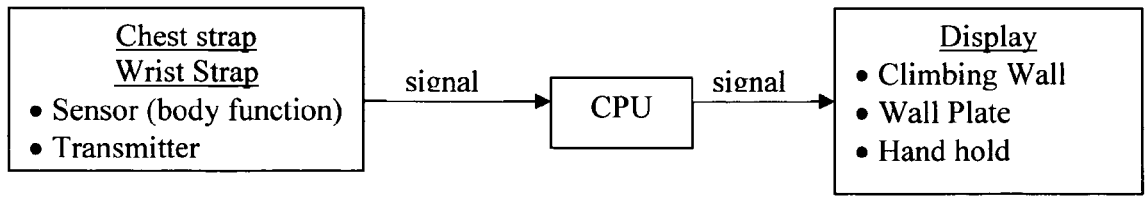
FIG. 7 is a block diagram of a heart rate sensor and display assembly using a computer to aggregate body function data.

The body function monitors and displays of the invention are functionally shown in the block diagrams of FIGS. 5-7. In FIG. 5 a chest strap is identified having a sensor and a transmitter. Chest straps are known in the art and are worn in proximity of the heart to detect a heart beat and to transmit a signal via a direct connection or a wire frequency to a display. The display as discussed above may be disposed in the climbing wall structure itself, in a wall plate mounted to the climbing wall or in a hand hold mounted to the climbing wall.

In FIG. 6 the block diagrams show a wrist strap identified having a sensor to monitor a body function such as a heartbeat, and a transmitter. Wrist straps are known in the art to be worn about the wrist to detect the pulse or heart beat and to transmit a signal via direct connection or wire frequency to a display. The display may be mounted in connection with the climbing wall structure, a wall plate and/or a handhold.

In FIG. 7, the block diagrams show both a chest strap and wrist strap identified having a sensor and transmitter and sending a signal to a central processing unit or computer which via hardware/software stores, analyzes body function data and transmits predetermined data, such as pulse rate, to a display on a climbing wall, wall plate or hand hold structure. The computer may have input data specific to a particular climber, for example, high and low limits for heart rate, blood pressure, etc., so that the display readily communicates this data to the climber during activity. An alarm may also be incorporated into the monitor and display assemblies of the present invention.

In summary, the heart rate display may be housed in the heart rate hand hold, or mounted to the surface of the climbing wall. As is known, "watch style" heart rate monitors exist and may be utilized within the scope of the invention. For example, a watch sensor and/or display may be attached to a hand hold or to the climbing wall and would function in the same way as described above. The various sensor and display devices of the invention are constructed to communicate with each other, having the appropriate electronics and power means, for example, incorporated into the climbing wall assembly, i.e., wireless data transmitters and receivers or wires connecting the sensors and the displays and incorporated into the wall structures, wall plates and handholds.

Additional features may also be provided in the heart rate hand hold. For example, a sensor may be placed into a heart rate hand hold to receive heart rate data. Pulse sensors may also be mounted on or contained in the climbing wall and/or mounted on or contained in the wall plates used on climbing walls. This utilization is similar to the Insta-Pulse® monitor that quickly displays a heart rate when grasped or when appropriate contact is made. The heart rate hand hold may also provide additional features provided in "watch-style" monitors, for example, a stopwatch, calorie expenditure data, heart rate zone high/low limit alarm, etc.

Insta-Pulse® monitors are fitness heart rate monitors sold by Biosig Instruments, Inc. These monitors may be portable or mounted structures that are grasped with both hands, and which are typically used during aerobic, jogging or walking exercises and do not require a chest strap attachment. The sensor, display and associated electronics of these monitors are exemplary of the monitor and display systems of the present invention. For example, the heart rate modules and associated computer equipment may be used in the sensors, displays and systems of the climbing wall structures, hand holds and route plates of the invention. In the present invention it is preferred that body function data, such as heart rate, be obtained via the touching of one hand and, thus, prior art monitor electronics allowing such use may be incorporated into the present invention.

As many changes are possible to the heart rate monitor and display devices of this invention, utilizing the teachings thereof, the description above and the accompanying drawings should be interpreted in the illustrative and not the limited sense.

That which is claimed is:

1. A monitor device for a climbing wall assembly comprising:
   a) a climbing wall structure having a plurality of hand holds extending therefrom;
   b) at least one said hand holds having a body structure with a sensor device to detect a climber's body function data, said sensor device being constructed to monitor the heart rate of the climber; and
   c) a display device located on said climbing wall structure showing the body function data, said display device being constructed to show the heart rate of the climber.

2. The monitor device of claim 1, wherein said body structure of said at least one hand hold includes a flat mounting surface and a curved grabbing surface and wherein said sensor device has a sensing surface, said sensing surface being generally flush with and integral said curved grabbing surface of said handhold body so that a climber contacts the curved sensing surface when grabbing said handhold.

3. The monitor device of claim 2, wherein said sensor device is mounted to the exterior surface of the hand hold.

4. The monitor device of claim 1, wherein a wall plate structure is mounted to said climbing wall structure and wherein said display device is contained in said wall plate structure.

5. The monitor device of claim 1, wherein a computer device is provided to record, store and analyze the body function data of the climber.

6. The monitor device of claim 5, wherein said computer device has input means for receiving a high and low limit of a climber's body function data and wherein an alarm is provided when either the high or low limit is reached.

7. The monitor device of claim 1, wherein a chest or wrist strap having a sensor and transmitter is provided for use by the climber to monitor the climber's body functions.

8. The monitor device of claim 1, wherein said at least one hand hold has a cavity and a protrusion and wherein said display device is positioned in said cavity and wherein a wrist watch with a sensor and display is positioned about said protrusion.

9. A heart rate sensing and display system for use with a climbing wall assembly comprising:
   a) a climbing wall assembly having an exterior wall surface and at least one hand hold structure thereon having a body having a generally flat mounting surface and a curved grabbing surface extending therefrom, said curved grabbing surface having a contour;
   b) heart rate sensing means for sensing a user's pulse data which produces a signal containing sensed pulse data, said heart rate sensing means being located on said at least one hand hold and having a sensing surface which is generally flush with and having generally the same contour as said curved grabbing surface of said at least one handhold; and
   c) heart rate display means located either on said exterior wall surface of said climbing wall assembly or on at least one hand hold visible to the climber, said heart rate display means receiving said signal containing said sensed pulse data and displaying said sensed pulse data.

10. The heart rate sensing and display system of claim 9, wherein said system further includes a heart rate sensing means located on a watch worn by a user.

11. The heart rate sensing and display system of claim 9, wherein said climbing wall assembly further includes a wall plate and wherein said heart rate sensing means is located on said wall plate.

12. The heart rate sensing and display system of claim 9, wherein said climbing wall assembly further includes a wall plate and wherein said heart rate display means is located on said wall plate.

13. The heart rate sensing and display system of claim 9, wherein said heart rate display means is located on a wall panel of said climbing wall assembly.

14. The heart rate sensing and display system of claim 9, wherein a computer interface system is utilized to aggregate a climber's heart rate data over time.

15. A monitoring and display system for climbing wall assemblies comprising:
   a) a climbing wall structure having a plurality of hand holds defining at least one climbing route having a beginning and an end;
   b) a sensor structure incorporated into at least two said hand holds, said sensor structure being constructed and arranged to detect body function data of a climber and having signal transmitting means;
   c) a display structure incorporated into either said climbing wall structure or at least one said hand hold structure, said display structure being constructed and arranged to receive a signal from said sensor structure transmitting means to visually show said body function data; and
   d) a computer device to record, store and analyze said body function data and having input means for receiving a high and low limit of a climber's body function data and wherein an alarm is provided when either said high or low limit is reached.

16. The monitoring and display system of claim 15, wherein said sensor structure is constructed to monitor the heart rate of the climber, wherein said display structure is constructed to show the heart rate of the climber and further wherein a sensor structure is disposed in a hand hold at the beginning and end of said climbing route.

17. The monitoring and display system of claim 15, wherein said sensor structure is incorporated into and integral with a hand hold and wherein said display structure is incorporated into another handhold which is visible to the climber along said at least one climbing route.

18. The monitoring and display system of claim 17, wherein a wall plate structure is mounted to said climbing wall structure, wherein said wall plate structure has magnetic or metallic properties and wherein said display structure is contained in said wall plate structure or magnetically held to said wall plate structure.

* * * * *